US012588817B2

(12) United States Patent
Maximo et al.

(10) Patent No.: US 12,588,817 B2
(45) Date of Patent: *Mar. 31, 2026

(54) SYSTEMS AND METHODS FOR GENERATING DIAGNOSTIC SCAN PARAMETERS FROM CALIBRATION IMAGES

(71) Applicant: GE Precision Healthcare LLC, Milwaukee, WI (US)

(72) Inventors: André De Almeida Maximo, Rio de Janeiro (BR); Dattesh Dayanand Shanbhag, Bangalore (IN); Chitresh Bhushan, Schenectady, NY (US); Dawei Gui, Sussex, WI (US)

(73) Assignee: GE PRECISION HEALTHCARE LLC, Milwaukee, WI (US)

( * ) Notice: Subject to any disclaimer, the term of this patent is extended or adjusted under 35 U.S.C. 154(b) by 1438 days.

This patent is subject to a terminal disclaimer.

(21) Appl. No.: 16/711,120

(22) Filed: Dec. 11, 2019

(65) Prior Publication Data

US 2021/0177295 A1    Jun. 17, 2021

(51) Int. Cl.
| | |
|---|---|
| *A61B 5/00* | (2006.01) |
| *G01R 33/54* | (2006.01) |
| *G06T 7/00* | (2017.01) |

(52) U.S. Cl.
CPC .......... *A61B 5/0037* (2013.01); *G01R 33/543* (2013.01); *G06T 7/0012* (2013.01); *A61B 2576/00* (2013.01)

(58) Field of Classification Search
CPC .... G01R 33/58; G01R 33/543; A61B 5/0073; A61B 5/005; A61B 5/055
See application file for complete search history.

(56) References Cited

U.S. PATENT DOCUMENTS 8,190,232 B2 * 5/2012 Zhang .................... A61B 5/055
                                                                    600/407
11,506,739 B2 * 11/2022 Gui ...................... A61B 5/7264
(Continued)

OTHER PUBLICATIONS

JD Elster, "Performing an MR Scan," Nov. 2019, Questions and Answers in MRI, MRIQuestions.com, Retrieved from https://mriquestions.com/what-are-the-steps.html (Year: 2019).*
(Continued)

*Primary Examiner* — Keith M Raymond
*Assistant Examiner* — Johnathan Maynard
(74) *Attorney, Agent, or Firm* — McCoy Russell LLP

(57) ABSTRACT

Methods and systems are provided for determining diagnostic-scan parameters for a magnetic resonance (MR) diagnostic-scan, from MR calibration images, enabling acquisition of high-resolution diagnostic images of one or more anatomical regions of interest, while bypassing acquisition of localizer images, increasing a speed and efficiency of MR diagnostic-scanning. In one embodiment, a method for a magnetic resonance imaging (MRI) system comprises, acquiring a magnetic resonance (MR) calibration image of an imaging subject, mapping the MR calibration image to a landmark map using a trained deep neural network, determining one or more diagnostic-scan parameters based on the landmark map, acquiring an MR diagnostic image according to the diagnostic-scan parameters, and displaying the MR diagnostic image via a display device.

7 Claims, 10 Drawing Sheets
(2 of 10 Drawing Sheet(s) Filed in Color)

(56) References Cited

U.S. PATENT DOCUMENTS

| | | | | |
|---|---|---|---|---|
| 2013/0279779 | A1* | 10/2013 | Darrow | A61B 5/055 |
| | | | | 382/131 |
| 2014/0364720 | A1* | 12/2014 | Darrow | G01R 33/543 |
| | | | | 600/410 |
| 2015/0012466 | A1* | 1/2015 | Sapiro | A61B 6/501 |
| | | | | 706/12 |
| 2015/0157207 | A1* | 6/2015 | Ikeda | A61B 5/055 |
| | | | | 600/407 |
| 2015/0260819 | A1* | 9/2015 | Lauer | G01R 33/5608 |
| | | | | 324/309 |
| 2016/0169996 | A1* | 6/2016 | Okuda | G01R 33/543 |
| | | | | 600/410 |
| 2016/0174919 | A1* | 6/2016 | Ahn | A61B 6/4417 |
| | | | | 382/131 |
| 2016/0216354 | A1* | 7/2016 | Wang | G01R 33/5635 |
| 2016/0300026 | A1* | 10/2016 | Bogoni | G06T 7/11 |
| 2017/0248669 | A1* | 8/2017 | Jasinschi | G01R 33/5608 |
| 2018/0025489 | A1* | 1/2018 | Tiwari | A61B 5/0037 |
| | | | | 600/420 |
| 2018/0153431 | A1* | 6/2018 | Amies | A61B 5/055 |
| 2018/0210053 | A1* | 7/2018 | Piron | G01R 33/543 |
| 2018/0228460 | A1* | 8/2018 | Singh | G01R 33/5608 |
| 2018/0256041 | A1* | 9/2018 | Dormer | A61B 5/7207 |
| 2018/0325482 | A1* | 11/2018 | Williams | G06T 7/0016 |
| 2019/0021625 | A1* | 1/2019 | Reda | G01R 33/543 |
| 2019/0355149 | A1* | 11/2019 | Avendi | A61B 34/20 |
| 2020/0037962 | A1* | 2/2020 | Shanbhag | A61B 5/055 |
| 2021/0118549 | A1* | 4/2021 | Sapiro | G16H 50/20 |

OTHER PUBLICATIONS

Martin Prince, "Exercise 3: Scanning an Human Using a Protocol," 2009, How to learn MRI: An Illustrated Workbook, Retrieved from http://web.archive.org/web/20141220144305/http://www.mrprotocols.com/learnmri/ (Year: 2009).*

JD Elster, "Automatic Prescan," Nov. 2019, Questions and Answers in MRI, MRIQuestions.com, Retrieved from https://mriquestions.com/automatic-prescan.html (Year: 2019).*

JD Elster, "SENSE/ASSET," Nov. 2019, Questions and Answers in MRI, MRIQuestions.com, Retrieved from https://mriquestions.com/senseasset.html (Year: 2019).*

Backus, C., & Folio, L. (2008). Radiology corner. Answer to last month's radiology case (# 26) and image: Lung laceration with loculated blood, active bleeding, contusion and hemothorax. Military Medicine, 173(8), xv-xvi. (Year: 2008).*

Hardesty, C. (2017). Explained: Neural Networks. MIT News, Retrieved from https://news.mit.edu/2017/explained-neural-networks-deep-learning-0414. (Year: 2017).*

Machine Learning. (2019). Wikipedia: The Free Encyclopedia. Retrieved from https://en.wikipedia.org/w/index.php?title=Machine_learning&oldid=928477695 (Year: 2019).*

Training, validation, and test data sets. (2019). Wikipedia: The Free Encyclopedia. Retrieved from https://en.wikipedia.org/w/index.php?title=Training,_validation,_and_test_data_sets&oldid=928158908 (Year: 2019).*

Dawkins, P. (2018). Section 1-3: Equations of Planes. Paul's Online Notes: Calculus III. Retrieved from https://tutorial.math.lamar.edu/classes/calciii/eqnsofplanes.aspx. (Year: 2018).*

Lundervold, A. S., & Lundervold, A. (2019). An overview of deep learning in medical imaging focusing on MRI. Zeitschrift für Medizinische Physik, 29(2), 102-127. (Year: 2019).*

Gui, D. et al., "Systems and Methods for Generating Localizer Scan Settings From Calibration Images," U.S. Appl. No. 16/573,955, filed Sep. 17, 2019, 40 pages.

* cited by examiner

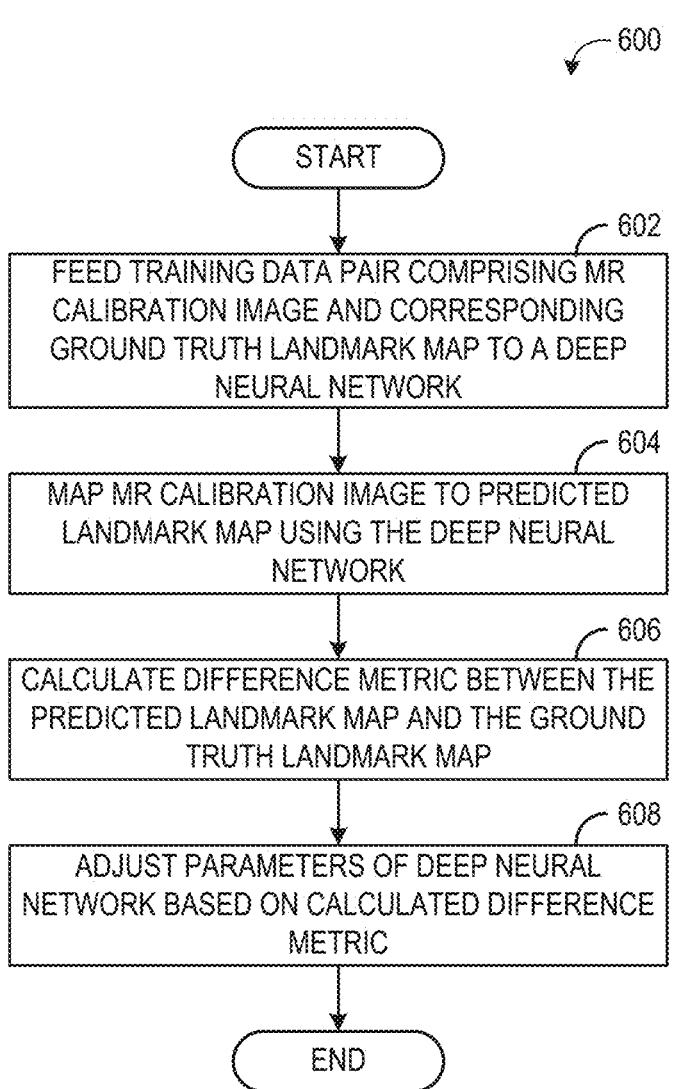

600

START

602

FEED TRAINING DATA PAIR COMPRISING MR CALIBRATION IMAGE AND CORRESPONDING GROUND TRUTH LANDMARK MAP TO A DEEP NEURAL NETWORK

604

MAP MR CALIBRATION IMAGE TO PREDICTED LANDMARK MAP USING THE DEEP NEURAL NETWORK

606

CALCULATE DIFFERENCE METRIC BETWEEN THE PREDICTED LANDMARK MAP AND THE GROUND TRUTH LANDMARK MAP

608

ADJUST PARAMETERS OF DEEP NEURAL NETWORK BASED ON CALCULATED DIFFERENCE METRIC

END

FIG. 6

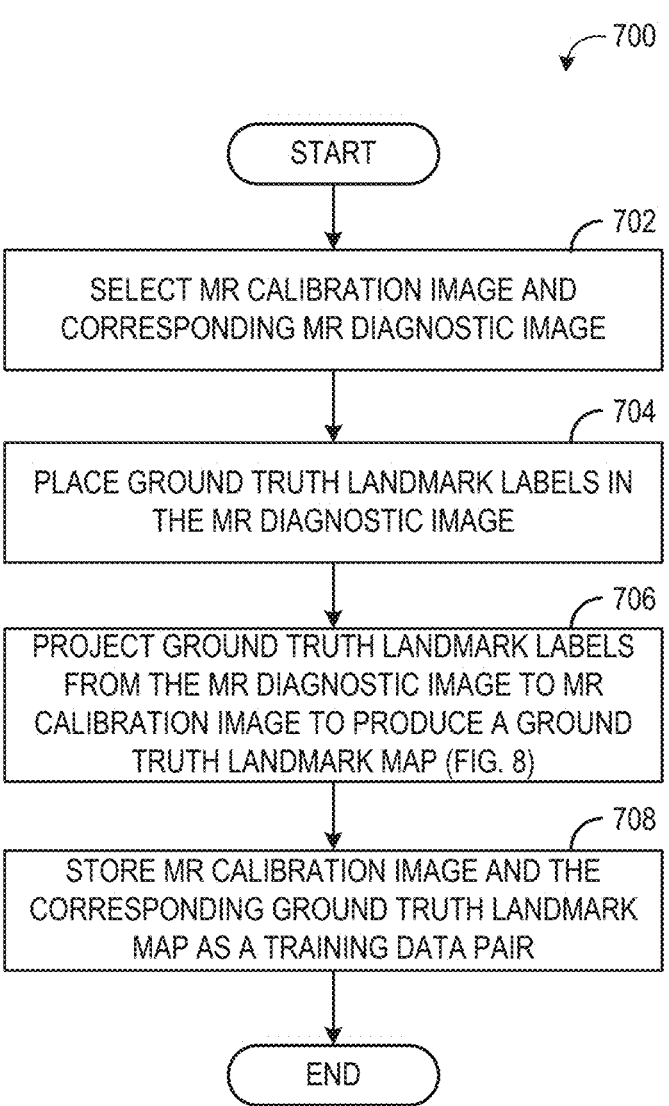

700

START

702
SELECT MR CALIBRATION IMAGE AND
CORRESPONDING MR DIAGNOSTIC IMAGE

704
PLACE GROUND TRUTH LANDMARK LABELS IN
THE MR DIAGNOSTIC IMAGE

706
PROJECT GROUND TRUTH LANDMARK LABELS
FROM THE MR DIAGNOSTIC IMAGE TO MR
CALIBRATION IMAGE TO PRODUCE A GROUND
TRUTH LANDMARK MAP (FIG. 8)

708
STORE MR CALIBRATION IMAGE AND THE
CORRESPONDING GROUND TRUTH LANDMARK
MAP AS A TRAINING DATA PAIR

END

FIG. 7

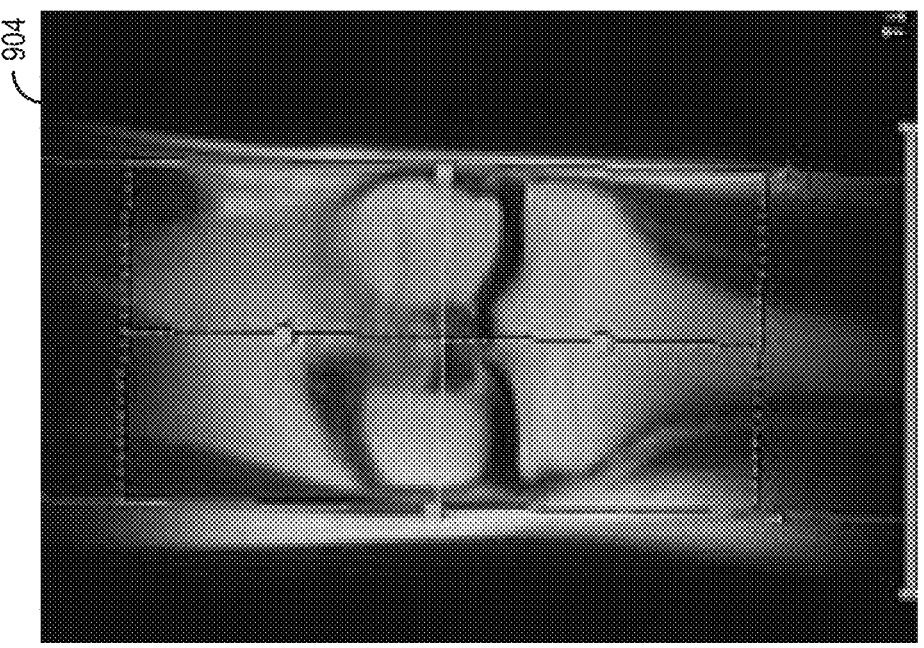
FIG. 9
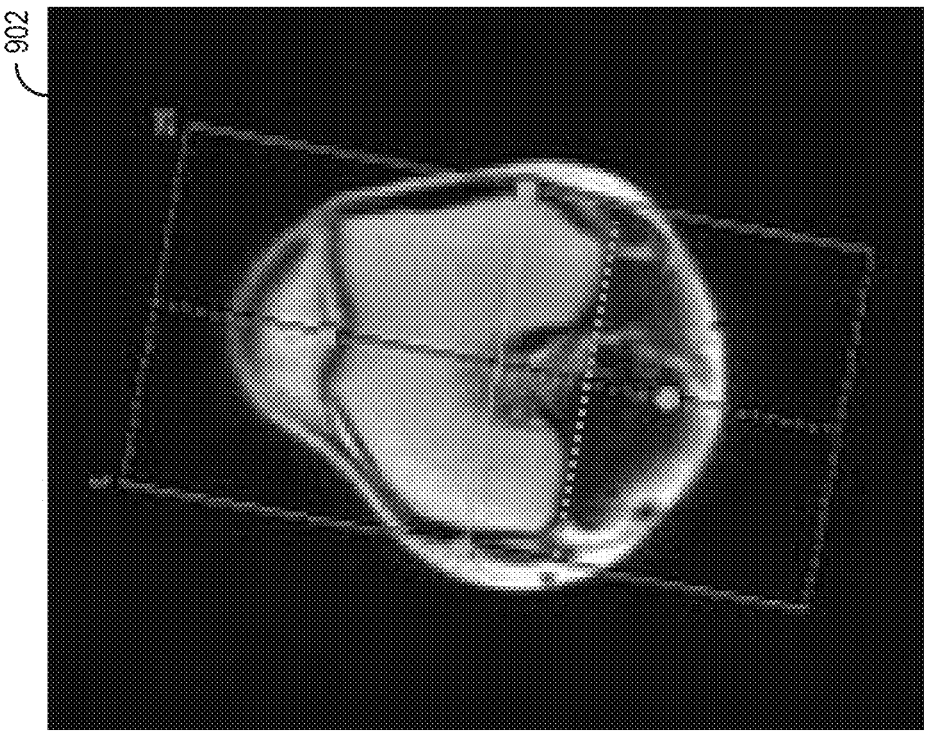

SYSTEMS AND METHODS FOR GENERATING DIAGNOSTIC SCAN PARAMETERS FROM CALIBRATION IMAGES

TECHNICAL FIELD

Embodiments of the subject matter disclosed herein relate to magnetic resonance imaging (MRI), and more particularly, to systems and methods for generating diagnostic-scan parameters from magnetic resonance (MR) calibration images using deep neural networks.

BACKGROUND

Medical imaging systems are often used to obtain internal physiological information of a subject, such as a patient. For example, a medical imaging system may be used to obtain images of the bone structure, the brain, the heart, the lungs, and various other features of a patient. Medical imaging systems may include magnetic resonance imaging (MRI) systems, computed tomography (CT) systems, x-ray systems, ultrasound systems, and various other imaging modalities.

In MRI, prior to performing a diagnostic-scan of a patient, a calibration image may be acquired in order to calibrate hardware settings of the MRI system. Calibration images are low resolution, large field-of-view (FOV), MR images, which may be acquired by a relatively short scan (5-10 seconds). Calibration images may have large intensity variations across the FOV due to radiofrequency coil related shading, resulting in images lacking detailed anatomical information. Conventionally, calibration images are used to adjust hardware settings of an MRI system, and for image intensity normalization. Calibration images may lack the resolution necessary for an operator of the MRI system to locate the anatomy of interest, which is to be imaged by a high-resolution diagnostic-scan. In conventional MRI protocols, determining a location of an anatomical region of interest to be imaged by a diagnostic-scan is accomplished using localizer images, which may have higher resolution than the calibration image(s).

Localizer images comprise moderately fast (approximately 30 seconds), anatomy location blinded, thick slice scans or low-dose scans of a patient. The medical imaging system and/or operator of the medical imaging system may plan the diagnostic-scan of the subject according to the localizer images, to ensure that the diagnostic-scan of the subject correctly images the anatomical region of interest. If the localizer images do not adequately show the anatomical region of interest or display imaging artifacts, the patient or the localizer scan parameters may be adjusted within the bore of the MRI system, and the localizer scan may be repeated until the anatomical region of interest is sufficiently clear within the localizer images for the MRI system operator to plan the diagnostic-scan. This process may prolong the total duration of MRI. Therefore, it is generally desirable to explore new approaches for more rapidly and consistently locating an anatomical region of interest to be diagnostically imaged using MRI.

SUMMARY

The inventors herein have identified systems and methods which may enable determination of diagnostic-scan parameters using calibration images, bypassing the need to acquire localizer images. In one embodiment, a method for a magnetic resonance imaging (MRI) system comprises, acquiring a magnetic resonance (MR) calibration image of an imaging subject, mapping the MR calibration image to a landmark map using a trained deep neural network, determining one or more diagnostic-scan parameters based on the landmark map, acquiring an MR diagnostic image according to the diagnostic-scan parameters, and displaying the MR diagnostic image via a display device. In this way, an MRI system may determine diagnostic-scan parameters by leveraging MR calibration images using deep neural networks, which may reduce a total duration of MRI diagnostic-scanning, by bypassing acquisition of localizer images. Further, landmark data included in the landmark map may enable automatic in-line reformatting of acquired MR images, to show one or more anatomical regions of interest in one or more predetermined orientations.

The above advantages and other advantages, and features of the present description will be readily apparent from the following Detailed Description when taken alone or in connection with the accompanying drawings. It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The patent or application file contains at least one drawing executed in color. Copies of this patent or patent application publication with color drawing(s) will be provided by the office upon request and payment of the necessary fee.

Various aspects of this disclosure may be better understood upon reading the following detailed description and upon reference to the drawings in which:

FIG. 6 is a flow chart illustrating a method for training a deep neural network to predict a landmark map from MR calibration images, according to an exemplary embodiment;

FIG. 7 is a flow chart illustrating a method for generating training data for the deep neural network of FIG. 3, according to an exemplary embodiment;

FIG. 9 shows examples of diagnostic-scan region previews, which may be displayed to a user, according to an exemplary embodiment;

Figure 1:
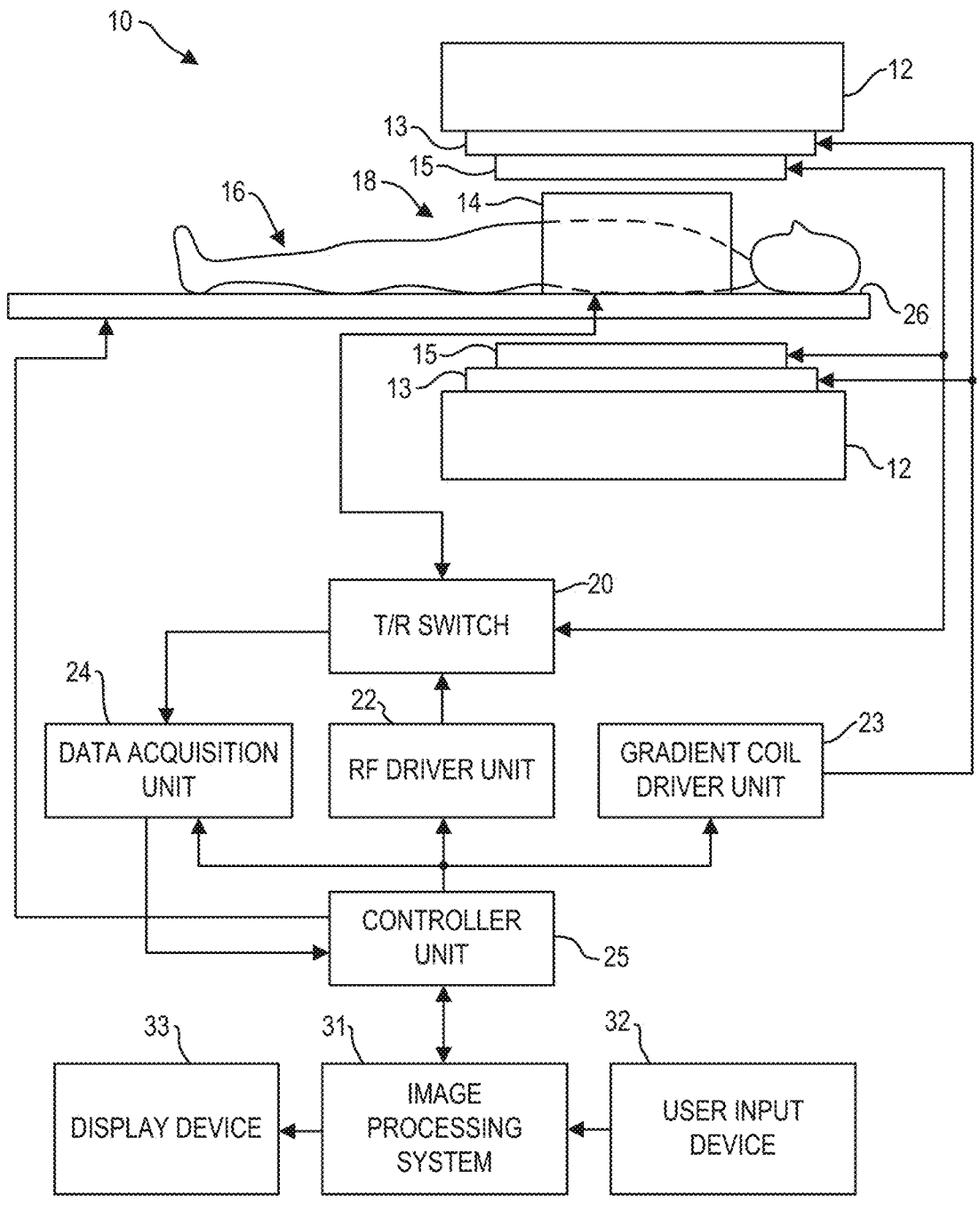
FIG. 1 shows a block diagram of an exemplary embodiment of an MRI system.

The drawings illustrate specific aspects of the described systems and methods for determining diagnostic-scan parameters from MR calibration images, using deep neural networks. Together with the following description, the drawings demonstrate and explain the structures, methods, and principles described herein. In the drawings, the size of components may be exaggerated or otherwise modified for clarity. Well-known structures, materials, or operations are not shown or described in detail to avoid obscuring aspects of the described components, systems and methods.

DETAILED DESCRIPTION

The following description relates to systems and methods for mapping MR calibration images to landmark maps, and acquiring one or more diagnostic images using diagnostic-scan parameters determined using the landmark maps. MR calibration images are routinely acquired prior to diagnostic imaging of patient anatomical regions, and are used in selecting surface coil elements, measuring surface coil sensitivities to correct signal shadings, and/or accelerating data acquisition. The current disclosure enables additional use to be made of calibration images, by automatically labeling one or more landmarks/regions of interest within a calibration image using a trained deep neural network, and determining one or more diagnostic-scan parameters (e.g., diagnostic-scan plane position/orientation/thickness, coverage, etc.) based on the labeled landmarks/regions of interest. The diagnostic-scan parameters determined in this manner may be used to acquire one or more diagnostic images, bypassing the need to acquire localizer images. As localizer image acquisition and planning may take up to 5 minutes, bypassing localizer image acquisition may substantially reduce a total MR scan time, and reduce patient discomfort.

The current disclosure teaches mapping MR calibration images to landmark maps using trained deep neural networks, wherein landmark maps may indicate one or more of a position, a center point, an orientation, a size/extent, a shape, and an anatomical classification/identification of one or more landmarks included in the MR calibration image, and one or more diagnostic-scan planes/volumes may be determined based on this information. In one embodiment, a landmark map may be used to select a coverage, a location, an orientation and other parameters of a diagnostic-scan plane/volume, such that the scan plane/volume captures an anatomical region of interest spatially related to the one or more landmarks included in the landmark map. In one embodiment, a landmark map is used to determine the position of a scan box, wherein a scan box indicates a region to be diagnostically scanned, and includes information regarding a number of planes/slices, including slice position orientation, thickness, spacing, etc.

The disclosure further provides for automatic in-line reformatting of acquired high-resolution, isotropic, three-dimensional (3D) MR images, using the landmark information included in the landmark map. In one embodiment, a location and coverage of a high-resolution, 3D, isotropic, MR image may be planned based on one or more labeled landmarks included in a landmark map, and following acquisition of the 3D isotropic MR image, one or more two-dimensional (2D) image slices may be produced from the 3D isotropic MR image based on landmark information included in the landmark map.

In one embodiment, the current disclosure may enable automation of MRI graphical prescriptions (AutoGRx) using MR calibration images without use of localizer images that are routinely used in clinical practices. The current disclosure makes use of MR calibration images with large FOV to generate diagnostic-scan parameters which may be used while acquiring high resolution images for a given set of landmark(s). The current disclosure enables moving the graphical prescription to the pre-scan stage, reducing the number of MRI system operator inputs needed to plan and initiate a diagnostic-scan of a patient. The ability to determine diagnostic-scan parameters without localizer images may be particularly useful in diagnostic-scanning of flexible anatomical regions, such as during musculoskeletal exams, where localizers are often repeated due to poor anatomical coverage (up to 50% of the time) leading to wasted scan time and patient discomfort. The methods and systems disclosed herein may reduce scan time, while increasing diagnostic image consistency, as the approach can determine diagnostic-scan parameters to capture an anatomy region of interest using MR calibration images.

Further, the current disclosure provides for displaying a diagnostic-scan region preview to the MRI system operator, showing a region of the patient anatomy to be imaged, prior to execution of a diagnostic-scan, giving the MRI system operator the final say in determining whether or not to proceed with acquisition of a diagnostic image.

Figure 2:
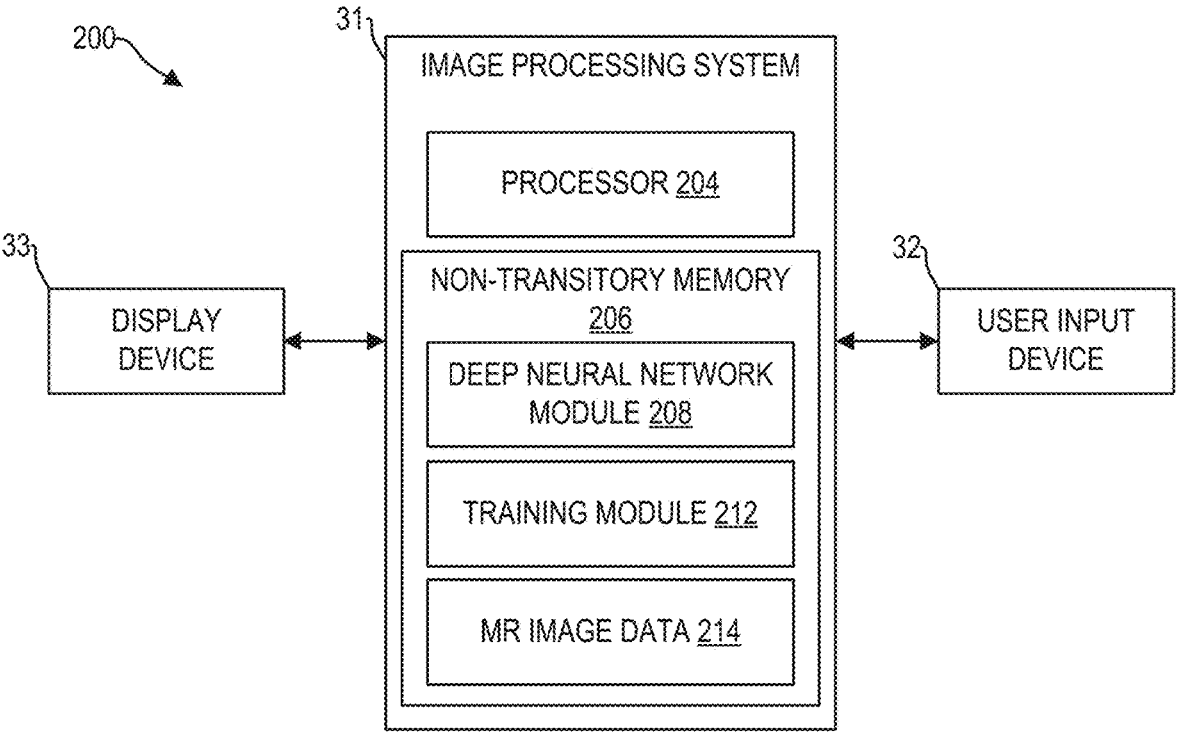
FIG. 2 is a schematic diagram illustrating a system for determining diagnostic-scan parameters from MR calibration images, according to an exemplary embodiment.

In one embodiment, an MR calibration image acquired by an MRI system (such as the MRI system of FIG. 1) may be processed by an image processing system, such as the image processing system 31 shown in FIG. 2. The image processing system 31 may comprise a deep neural network stored in non-transitory memory, such as the deep neural network illustrated schematically in FIG. 3, which may be deployed to determine a landmark map for an MR calibration image. The image processing system and MRI system may execute a diagnostic-scanning method, such as method 400 shown in FIG. 4, wherein an MR calibration image is acquired by the MRI system, mapped to a landmark map using a trained deep neural network in substantially real time, and a diagnostic image is acquired according to diagnostic-scan parameters determined using the landmark map. In some embodiments, as part of method 400, a diagnostic-scan region preview, such as first scan region preview 902 and/or second scan region preview 904, shown in FIG. 9, may be displayed to an MRI system operator prior to diagnostic-scanning, as indicated at operation 408 of method 400.

Figure 5:
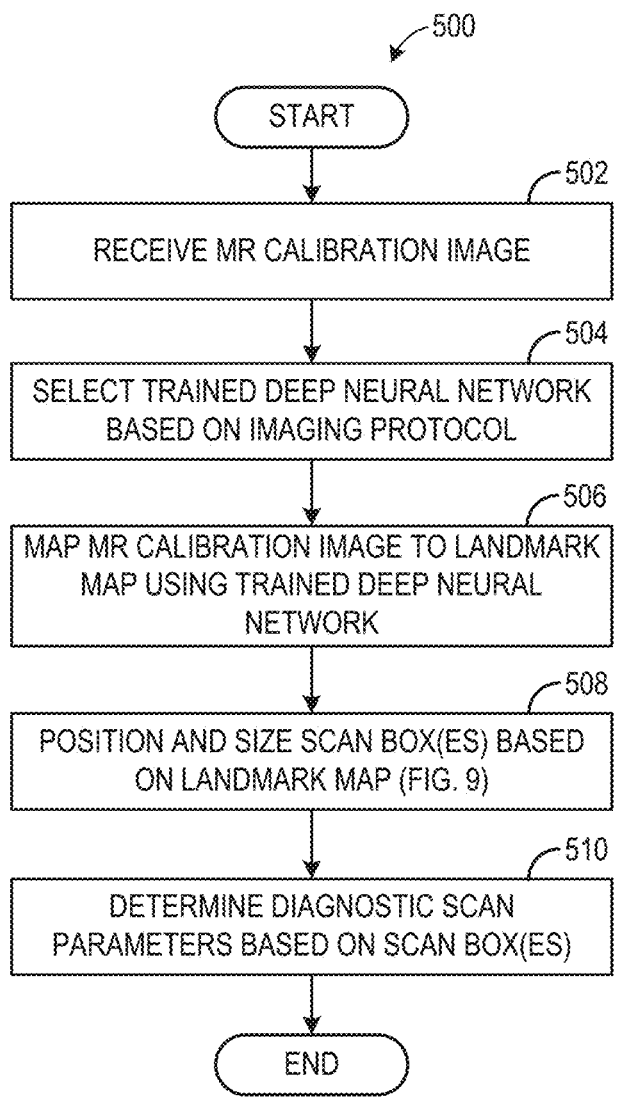
FIG. 5 is a flow chart illustrating a method for mapping an MR calibration image to a landmark map using a trained deep neural network, and determining diagnostic-scan parameters from the landmark map, according to an exemplary embodiment.

Method 500, shown in FIG. 5, shows a more detailed flowchart of a method for determining diagnostic-scan parameters using MR calibration images. Method 500 may be executed as part of method 400, as indicated at operation 406. Method 500 includes selecting a trained deep neural network based on a current imaging protocol, mapping an MR calibration image to a corresponding landmark map using the trained deep neural network, positioning/sizing a scan box within the MR calibration image based on the landmark map, and determining one or more diagnostic-scan parameters based on the position/size of the scan box relative to the MR calibration image.

Figure 4:
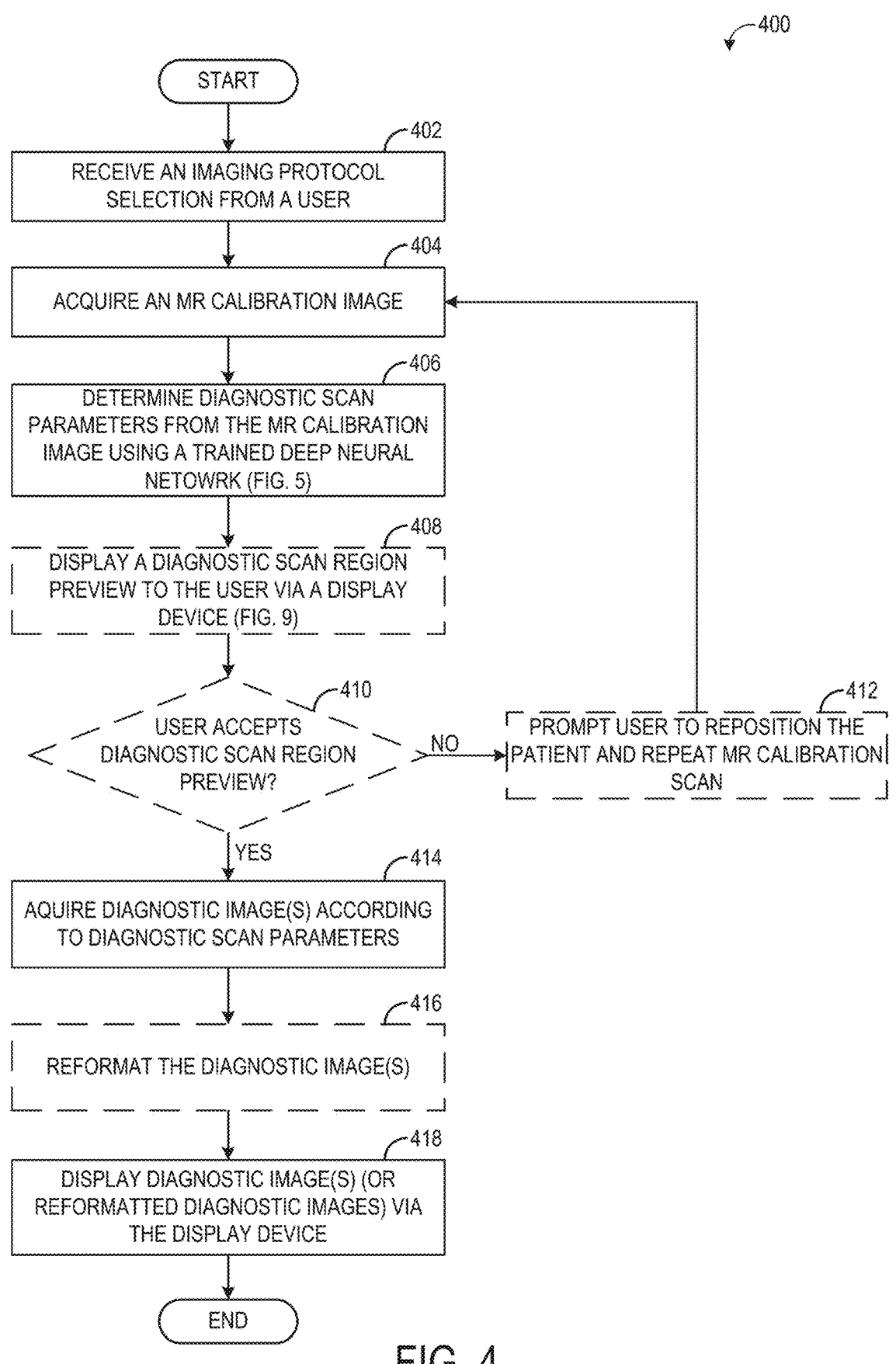
FIG. 4 is a flow chart illustrating a method for determining diagnostic-scan parameters based on an MR calibration image, according to an exemplary embodiment.
Figure 8:
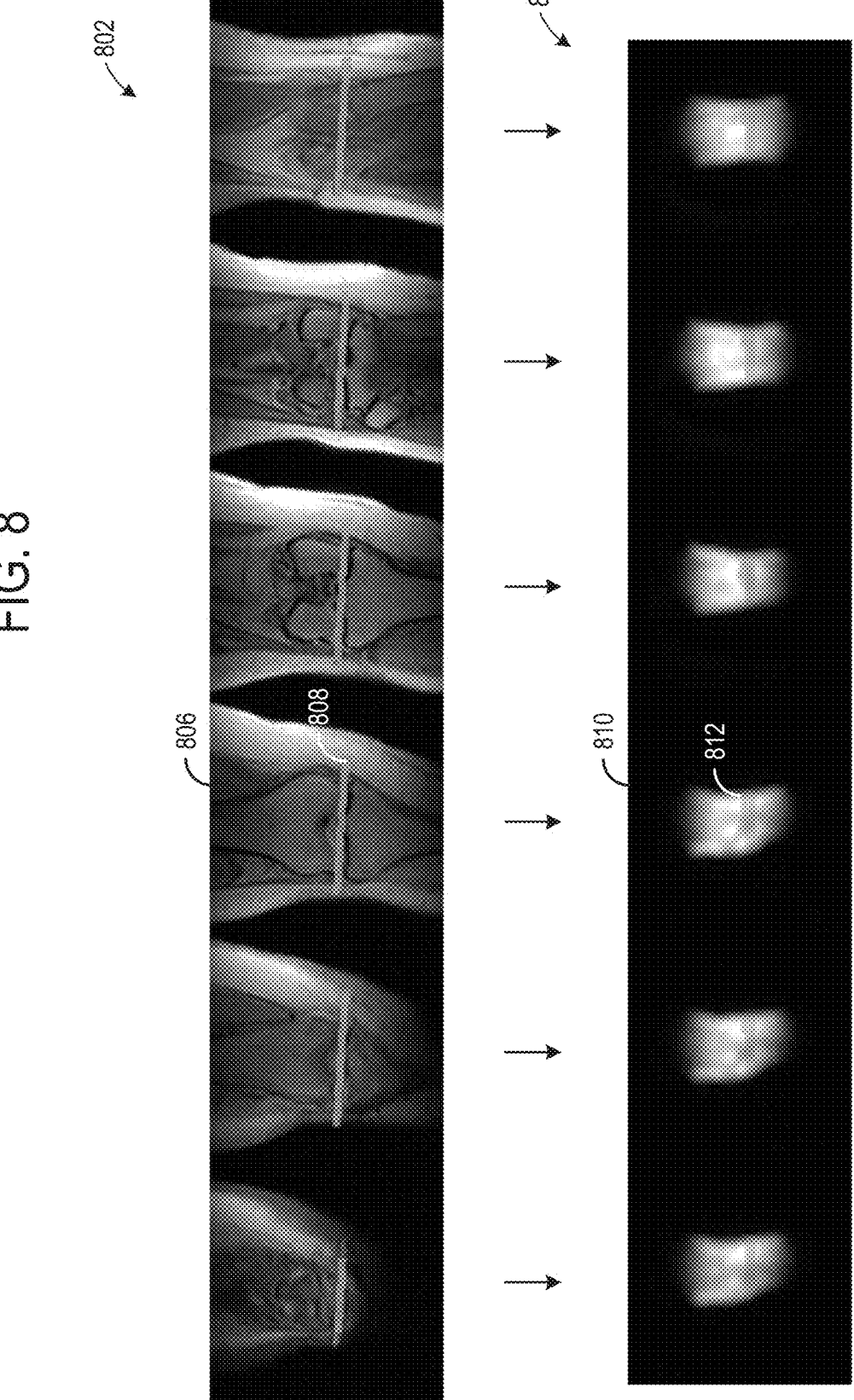
FIG. 8 shows example high-resolution MR images with landmark labels and corresponding calibration images, wherein the landmark labels from the high-resolution MR images are projected onto the calibration images, according to an exemplary embodiment.

The trained deep neural network used to map MR calibration images to landmark maps in FIGS. 4 and 5, may be trained using the method of FIG. 6, wherein training data pairs comprising MR calibration images and corresponding ground-truth landmark maps, are used to adjust parameters of the deep neural network according to a backpropagation algorithm. The training data pairs may be generated by placing landmark labels in high-resolution MR images, and projecting the landmark labels to corresponding (low reso-lution) MR calibration images, as discussed below, with reference to FIG. 7. FIG. 8 shows examples of ground-truth landmark maps produced by using the projection approach of FIG. 7.

Figure 10:
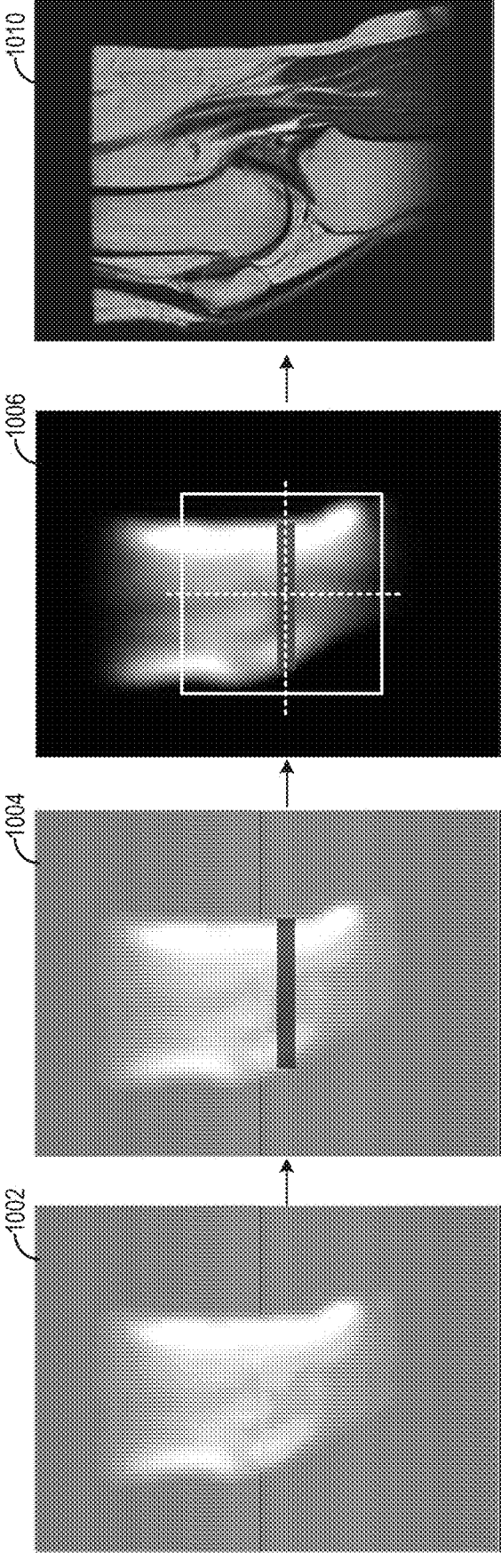
FIG. 10 shows an example of an MR calibration image, a corresponding landmark map, a scan box positioned within the MR calibration image based on the landmark map, and an MR diagnostic image acquired using diagnostic-scan parameters determined based on the scan box.

FIG. 10 shows one example of an MR calibration image, a landmark map of the MR calibration image, a scan box placed based on the landmark map, and a diagnostic image acquired according to diagnostic-scan parameters deter-mined based on the scan box.

It will be appreciated that the term landmark map, land-mark maps, and other similar terms used herein, may be used interchangeably with the term landmark plane, and land-mark plane mask, wherein both landmark map and landmark plane refer to an identified region in an MR calibration image, wherein, in some embodiments, the region may comprise a cloud of points, and/or an analytical expression mathematically describing the identified region (e.g., a plane equation).

Referring now to FIG. 1, MRI system 10 is shown. MRI system 10 includes a magnetostatic field magnet unit 12, a gradient coil unit 13, an RF coil unit 14, an RF body or volume coil unit 15, a transmit/receive (T/R) switch 20, an RF driver unit 22, a gradient coil driver unit 23, a data acquisition unit 24, a controller unit 25, a patient table or bed 26, an image processing system 31, a user input device 32, and a display device 33. In some embodiments, the RF coil unit 14 is a surface coil, which is a local coil typically placed proximate to the anatomy of interest of a subject 16. Herein, the RF body coil unit 15 is a transmit coil that transmits RF signals, and the local surface RF coil unit 14 receives the MR signals. As such, the transmit body coil (e.g., RF body coil unit 15) and the surface receive coil (e.g., RF coil unit 14) are separate but electromagnetically coupled compo-nents. The MRI system 10 transmits electromagnetic pulse signals to the subject 16 placed in an imaging space 18 with a static magnetic field formed to perform a scan for obtain-ing magnetic resonance signals from the subject 16. One or more MR images of the subject 16 can be reconstructed based on the magnetic resonance signals thus obtained by the scan.

The magnetostatic field magnet unit 12 includes, for example, an annular superconducting magnet, which is mounted within a toroidal vacuum vessel. The magnet defines a cylindrical space surrounding the subject 16 and generates a constant primary magnetostatic field $B_0$.

The MRI system 10 also includes a gradient coil unit 13 that forms a gradient magnetic field in the imaging space 18 so as to provide the magnetic resonance signals received by the RF coil arrays with three-dimensional positional infor-mation. The gradient coil unit 13 includes three gradient coil systems, each of which generates a gradient magnetic field along one of three spatial axes perpendicular to each other, and generates a gradient field in each of a frequency encod-ing direction, a phase encoding direction, and a slice selec-tion direction in accordance with the imaging condition. More specifically, the gradient coil unit 13 applies a gradient field in the slice selection direction (or scan direction) of the subject 16, to select the slice; and the RF body coil unit 15 or the local RF coil arrays may transmit an RF pulse to a selected slice of the subject 16. The gradient coil unit 13 also applies a gradient field in the phase encoding direction of the subject 16 to phase encode the magnetic resonance signals from the slice excited by the RF pulse. The gradient coil unit 13 then applies a gradient field in the frequency encoding direction of the subject 16 to frequency encode the magnetic resonance signals from the slice excited by the RF pulse.

The RF coil unit 14 is disposed, for example, to enclose the region to be imaged of the subject 16. In some examples, the RF coil unit 14 may be referred to as the surface coil or the receive coil. In the static magnetic field space or imaging space 18 where a static magnetic field $B_0$ is formed by the magnetostatic field magnet unit 12, the RF coil unit 15 transmits, based on a control signal from the controller unit 25, an RF pulse that is an electromagnet wave to the subject 16 and thereby generates a high-frequency magnetic field, $B_1$. This excites a spin of protons in the slice to be imaged of the subject 16. The RF coil unit 14 receives, as a magnetic resonance signal, the electromagnetic wave generated when the proton spin thus excited in the slice to be imaged of the subject 16 returns into alignment with the initial magneti-zation vector. In some embodiments, the RF coil unit 14 may transmit the RF pulse and receive the MR signal. In other embodiments, the RF coil unit 14 may only be used for receiving the MR signals, but not transmitting the RF pulse.

The RF body coil unit 15 is disposed, for example, to enclose the imaging space 18, and produces RF magnetic field pulses orthogonal to the main magnetic field $B_0$ pro-duced by the magnetostatic field magnet unit 12 within the imaging space 18 to excite the nuclei. In contrast to the RF coil unit 14, which may be disconnected from the MRI system 10 and replaced with another RF coil unit, the RF body coil unit 15 is fixedly attached and connected to the MRI system 10. Furthermore, whereas local coils such as the RF coil unit 14 can transmit to or receive signals from only a localized region of the subject 16, the RF body coil unit 15 generally has a larger coverage area. The RF body coil unit 15 may be used to transmit or receive signals to the whole body of the subject 16, for example. Using receive-only local coils and transmit body coils provides a uniform RF excitation and good image uniformity at the expense of high RF power deposited in the subject. For a transmit-receive local coil, the local coil provides the RF excitation to the region of interest and receives the MR signal, thereby decreasing the RF power deposited in the subject. It should be appreciated that the particular use of the RF coil unit 14 and/or the RF body coil unit 15 depends on the imaging application.

The T/R switch 20 can selectively electrically connect the RF body coil unit 15 to the data acquisition unit 24 when operating in receive mode, and to the RF driver unit 22 when operating in transmit mode. Similarly, the T/R switch 20 can selectively electrically connect the RF coil unit 14 to the data acquisition unit 24 when the RF coil unit 14 operates in receive mode, and to the RF driver unit 22 when operating in transmit mode. When the RF coil unit 14 and the RF body coil unit 15 are both used in a single scan, for example if the RF coil unit 14 is configured to receive MR signals and the RF body coil unit 15 is configured to transmit RF signals, then the T/R switch 20 may direct control signals from the RF driver unit 22 to the RF body coil unit 15 while directing received MR signals from the RF coil unit 14 to the data acquisition unit 24. The coils of the RF body coil unit 15 may be configured to operate in a transmit-only mode or a transmit-receive mode. The coils of the local RF coil unit 14 may be configured to operate in a transmit-receive mode or a receive-only mode.

The RF driver unit 22 includes a gate modulator (not shown), an RF power amplifier (not shown), and an RF oscillator (not shown) that are used to drive the RF coils (e.g., RF coil unit 15) and form a high-frequency magnetic field in the imaging space 18. The RF driver unit 22 modulates, based on a control signal from the controller unit 25 and using the gate modulator, the RF signal received from the RF oscillator into a signal of predetermined timing having a predetermined envelope. The RF signal modulated by the gate modulator is amplified by the RF power amplifier and then output to the RF coil unit 15.

The gradient coil driver unit 23 drives the gradient coil unit 13 based on a control signal from the controller unit 25 and thereby generates a gradient magnetic field in the imaging space 18. The gradient coil driver unit 23 includes three systems of driver circuits (not shown) corresponding to the three gradient coil systems included in the gradient coil unit 13.

The data acquisition unit 24 includes a pre-amplifier (not shown), a phase detector (not shown), and an analog/digital converter (not shown) used to acquire the magnetic resonance signals received by the RF coil unit 14. In the data acquisition unit 24, the phase detector phase detects, using the output from the RF oscillator of the RF driver unit 22 as a reference signal, the magnetic resonance signals received from the RF coil unit 14 and amplified by the pre-amplifier, and outputs the phase-detected analog magnetic resonance signals to the analog/digital converter for conversion into digital signals. The digital signals thus obtained are output to the image processing system 31.

The MRI system 10 includes a table 26 for placing the subject 16 thereon. The subject 16 may be moved inside and outside the imaging space 18 by moving the table 26 based on control signals from the controller unit 25.

The controller unit 25 includes a computer and a recording medium on which a program to be executed by the computer is recorded. The program when executed by the computer causes various parts of the system to carry out operations corresponding to pre-determined scanning. The recording medium may comprise, for example, a ROM, flexible disk, hard disk, optical disk, magneto-optical disk, CD-ROM, or non-transitory memory card. The controller unit 25 is connected to the user input device 32 and processes the operation signals input to the user input device 32 and furthermore controls the table 26, RF driver unit 22, gradient coil driver unit 23, and data acquisition unit 24 by outputting control signals to them. The controller unit 25 also controls, to obtain a desired image, the image processing system 31 and the display device 33 based on operation signals received from the user input device 32.

The user input device 32 includes user input devices such as a touchscreen, keyboard, and a mouse. The user input device 32 is used by an MRI system operator, for example, to input such data as an imaging protocol, to accept or decline a scan region preview, and in some embodiments, to set a region where an imaging sequence is to be executed. The imaging protocol data, the scan region preview acceptance or declination, and the imaging sequence execution region are output to the controller unit 25.

The image processing system 31 includes a processor and non-transitory memory on which machine executable instructions may be stored, wherein the machine executable instructions may enable the processor to execute one or more of the steps of one or more of the methods herein disclosed. The image processing system 31 may be connected to the controller unit 25 and may perform data processing based on control signals received from the controller unit 25 or user input device 32. The image processing system 31 is also connected to the data acquisition unit 24 and generates spectrum data by applying various image processing operations to the magnetic resonance signals output from the data acquisition unit 24.

The image processing system 31 may determine diagnostic-scan parameters (e.g., diagnostic-scan field of view) based on the location of a landmark (also herein referred to as an anatomical region of interest) be imaged (e.g., the location relative to the isocenter of the bore of the MR imaging system), which may be automatically detected/labeled in a landmark map generated by a deep neural network based on the MR calibration images acquired by MRI system 10. MRI system 10 may acquire diagnostic images according to the diagnostic-scan parameters, and/or the imaging processing system 31 may use the location of the landmarks/anatomical region of interest to notify an operator of the MR system to manually adjust one or more diagnostic-scan parameters, such as RF coil position. In one example, image processing system 31 and MRI system 10 may execute such a method, which will be discussed in detail below with reference to FIGS. 4 and 5. Image processing system 31 may thereby determine diagnostic-scan parameters using rapidly acquired MR calibration images. Image processing system 31 may be further configured to display the calibration images, with one or more scan boxes overlaid thereon, via display device 33, to provide a diagnostic-scan region preview to an MRI system operator, prior to acquisition of one or more diagnostic images based on the position, size, and orientation, of the one or more scan boxes.

The display device 33 displays an image on the display screen of the display device based on control signals received from the controller unit 25. The display device 33 displays, for example, a diagnostic-scan region preview, and/or subsequent diagnostic MR images produced by the image processing system 31. Display device 33 may comprise a graphical user interface, wherein a user may interact with/input/alter one or more data fields via user input device 32. The display device 33 may display a two-dimensional (2D) slice image or three-dimensional (3D) image of the subject 16 generated by the image processing system 31.

During a scan, RF coil array interfacing cables (not shown in FIG. 1) may be used to transmit signals between the RF coils (e.g., RF coil unit 14 and RF body coil unit 15) and other aspects of the processing system (e.g., data acquisition unit 24, controller unit 25, and so on), for example to control the RF coils and/or to receive information from the RF coils. As explained previously, the RF body coil unit 15 is a transmit coil that transmits RF signals, and the local surface RF coil unit 14 receives the MR signals. More generally, RF coils are used to transmit RF excitation signals ("transmit coil"), and to receive the MR signals emitted by an imaging subject ("receive coil"). In some embodiments, the transmit and receive coils are a single mechanical and electrical structure, or array of structures, with transmit/receive mode switchable by auxiliary circuitry. In other examples, the transmit body coil (e.g., RF body coil unit 15) and the surface receive coil (e.g., RF coil unit 14) may comprise separate components.

Referring to FIG. 2, MR image processing system 200 is shown, in accordance with an exemplary embodiment. In some embodiments, MR image processing system 200 is incorporated into the MRI system. In some embodiments, at least a portion of MR image processing 200 is disposed at a device (e.g., edge device, server, etc.) communicably coupled to the MRI system via wired and/or wireless connections. In some embodiments, at least a portion of MR image processing system 200 is disposed at a separate device (e.g., a workstation) which can receive images from the MRI system or from a storage device which stores the images generated by the MRI system. MR image processing system 200 may comprise image processing system 31, user input device 32, and display device 33.

Image processing system 31 includes a processor 204 configured to execute machine readable instructions stored in non-transitory memory 206. Processor 204 may be single core or multi-core, and the programs executed thereon may be configured for parallel or distributed processing. In some embodiments, the processor 204 may optionally include individual components that are distributed throughout two or more devices, which may be remotely located and/or configured for coordinated processing. In some embodiments, one or more aspects of the processor 204 may be virtualized and executed by remotely-accessible networked computing devices configured in a cloud computing configuration.

Non-transitory memory 206 may store deep neural network module 208, training module 212, and MR image data 214. Deep neural network module 208 may include one or more trained and/or untrained deep neural networks, comprising a plurality of weights and biases, activation functions, loss functions, and instructions for implementing the one or more deep neural networks to receive MR calibration images and map the input MR calibration images to corresponding landmark maps, wherein the landmark maps may be used to determine diagnostic-scan parameters for acquiring high-resolution MR images of one or more anatomical regions of interest. In some embodiments, the landmark maps may comprise a segmented/labeled anatomical region of interest, and/or a segmented/labeled landmark, wherein the landmark is spatially related to the anatomical region of interest in the MR calibration image. For example, deep neural network module 208 may store instructions for implementing a neural network, such as convolutional neural network (CNN) 300, shown in FIG. 3. However, other architectures such as combinations of fully connected networks and CNNs or generative adversarial networks and their variants can be used as well. Deep neural network module 208 may include various deep neural network metadata pertaining to the trained and/or untrained networks. In some embodiments, the deep neural network metadata may include an indication of the training data used to train a deep neural network, a training method employed to train the deep neural network, an accuracy/validation score of the deep neural network, and a type of anatomy/imaging protocol for which the deep neural network may be applied.

Non-transitory memory 206 may further include training module 212, which comprises instructions for training one or more of the deep neural networks stored in deep neural network module 208. In one embodiment, the training module 212 may include gradient descent algorithms, loss functions, and rules for generating and/or filtering/selecting training data for use in training a particular deep neural network. Training module 212 may include instructions that, when executed by processor 204, cause MR image processing system 200 to conduct one or more of the steps of method 600, discussed in more detail below. In some embodiments, training module 212 includes instructions for receiving training data pairs from MR image data 214, which comprise pairs of MR calibration images and corresponding ground-truth landmark maps, for use in training one or more of the deep neural networks stored in deep neural network module 208. In some embodiments, training module 212 includes machine executable instructions, that when executed, cause the processor 204 to conduct one or more of the steps of method 700, shown in FIG. 7, to generate training data pairs using MR image data, such as may be stored in MR image data 214. In some embodiments, the training module 212 is not disposed at the MR image processing system 200, but is disposed remotely, and is communicably coupled with MR image processing system 200.

Non-transitory memory 206 may further store MR image data 214, which may comprise MR images captured by MRI system 10. In some embodiments, the MR image data 214 may include MR calibration images, labeled MR calibration images, diagnostic images (2D and/or 3D diagnostic images), landmark maps, ground-truth landmark maps, localizer images, etc. In some embodiments, MR calibration images and corresponding ground-truth landmark maps, including one or more labeled/segmented landmarks/anatomical regions of interest, which may be stored in an ordered format, such that each MR calibration image of an anatomical region of a subject is associated with a ground-truth landmark map of the same anatomical region of the same subject. In some embodiments, the ground-truth landmark maps may be a segmentation map, overlain as a mask on top of corresponding MR calibration images, discerning between landmark and non-landmark (e.g., background, non-landmark anatomical regions, noise, etc.), where this ground-truth mask may be obtained by method 700, discussed in more detail below in reference to FIG. 7.

In some embodiments, non-transitory memory 206 may include components disposed at two or more devices, which may be remotely located and/or configured for coordinated processing. In some embodiments, one or more aspects of the non-transitory memory 206 may include remotely-accessible networked storage devices configured in a cloud computing configuration.

MR image processing system 200 may further include user input device 32. User input device 32 may comprise one or more of a touchscreen, a keyboard, a mouse, a trackpad, a motion sensing camera, or other device configured to enable a user to interact with and manipulate data within image processing system 31. In some embodiments, user input device 32 enables an MRI system operator to input/ select an imaging protocol. In some embodiments, the MRI system operator may view a diagnostic-scan region preview via display device 33, and may accept or decline the diagnostic-scan region preview using user input device 32.

Display device 33 may include one or more display devices utilizing virtually any type of technology. In some embodiments, display device 33 may comprise a computer monitor, and may display diagnostic-scan region previews, MR calibration images, diagnostic images, scan boxes, landmark maps, etc. as part of one or more of the methods disclosed herein. Display device 33 may be combined with processor 204, non-transitory memory 206, and/or user input device 32 in a shared enclosure, or may be peripheral display devices and may comprise a monitor, touchscreen, projector, or other display device known in the art, which may enable a user to view MR images produced by an MRI system, and/or interact with various data stored in non-transitory memory 206.

It should be understood that MR image processing system 200 shown in FIG. 2 is for illustration, not for limitation. Another appropriate image processing system may include more, fewer, or different components.

Figure 3:
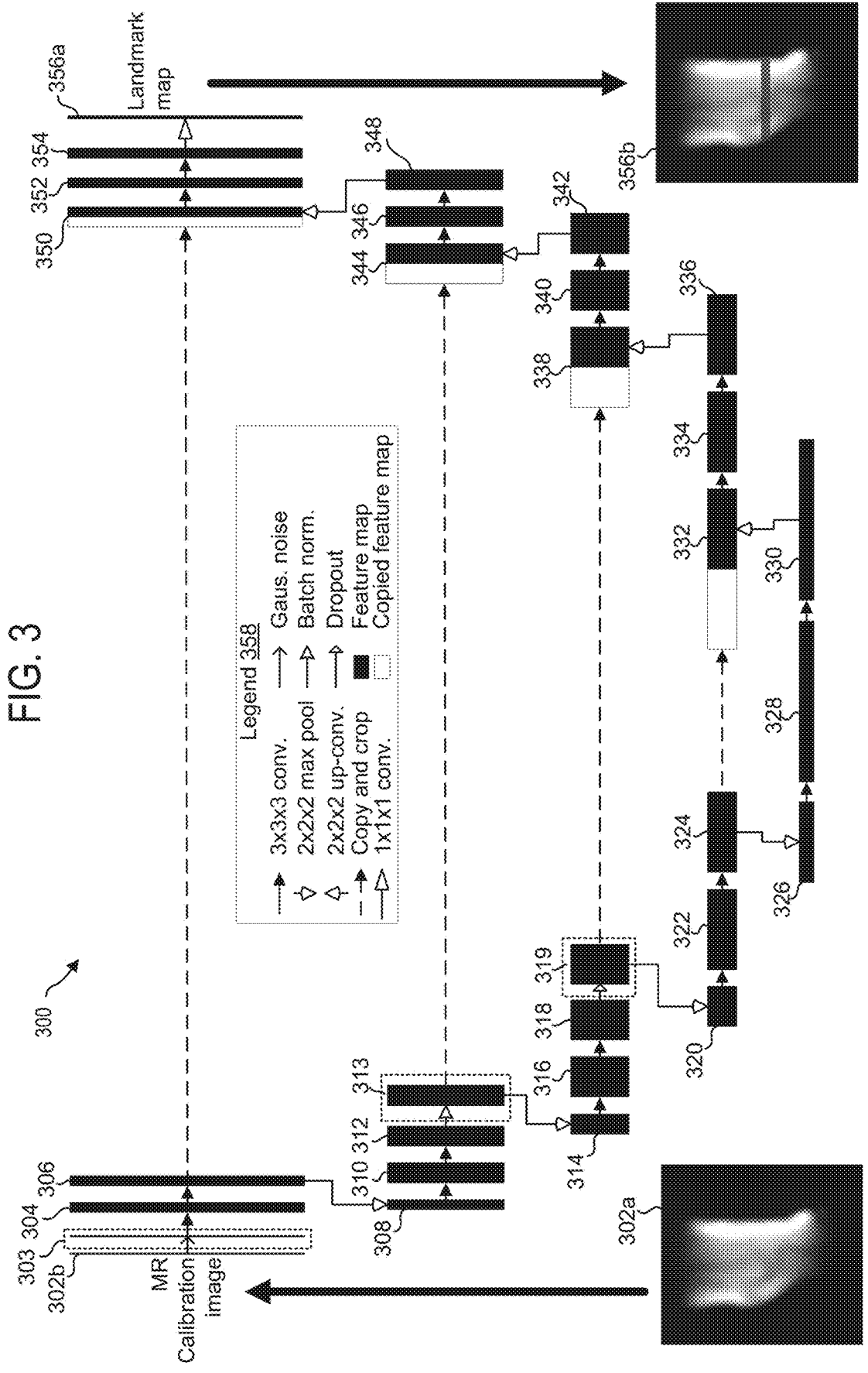
FIG. 3 is an architecture diagram of an exemplary deep neural network which can be used in the system of FIG. 2, according to an exemplary embodiment.

Turning to FIG. 3, an architecture diagram of CNN 300 is shown. CNN 300 may determine landmark maps from MR calibration images, wherein the landmark maps may be used to determine one or more diagnostic-scan parameters for a diagnostic-scan. In the description of FIG. 3, the landmark map (which may herein also be referred to as a landmark plane map) output from CNN 300 may comprise a segmentation map, wherein pixels/voxels classified as belonging to a pre-determined landmark, or landmark plane may be assigned a first value, and wherein pixels/voxels assigned to other landmarks or as non-landmarks, may be assigned a values different than the first value. In some embodiments, each of a plurality of distinct landmarks included in an input MR calibration image is mapped to a distinct binary segmentation map. In some embodiments, each of a plurality of landmarks included in an input MR calibration image may be mapped to a multi-label segmentation map, wherein each distinct landmark is labeled with a distinct value/identifier. In one embodiment, the landmark map comprises a multi-label segmentation may, wherein, for each pixel/voxel of an input MR calibration image, a class score, for each of a plurality of classes is determined, wherein the class score indicates a confidence of the given pixel/voxel belonging to each of the pre-determined classes. In some embodiments, the landmark map may be superimposed on an input MR calibration image to define the location and/or other attributes of the landmarks or landmark plane included therein (e.g., the boundaries of the landmarks, orientation of the landmark plane, and the center point of the landmark/landmark plane) within the imaging field of view (FOV) used to obtain the MR calibration image. CNN 300 represents a U-net architecture, which may be divided into an encoding portion (descending portion, elements 302*b*-330) and a decoding portion (ascending portion, elements 332-356*a*). CNN 300 is configured to receive an MR calibration image/volume of an anatomical region, comprising a plurality of voxels, and map the input MR calibration image to a landmark map/landmark plane. CNN architecture 300 includes a series of mappings, from an input image volume 302*b* which may be received by an input layer, through a plurality of feature maps, and finally to an output anatomical ROI location map 356*b*, which may be produced by an output layer 356*a*.

The various elements comprising CNN architecture 300 are labeled in legend 358. As indicated by legend 358, CNN architecture 300 includes a plurality of feature maps (and/or copied feature maps), wherein each feature map may receive input from either an external file, or a previous feature map, and may transform/map the received input to output to produce a next feature map. Each feature map may comprise a plurality of neurons, where in some embodiments, each neuron may receive input from a subset of neurons of a previous layer/feature map, and may compute a single output based on the received inputs, wherein the output may be propagated to a subset of the neurons in a next layer/feature map. A feature map may be described using spatial dimensions, such as length, width, depth, and hyper depth (which may correspond to features of each of voxel of the input image/volume), wherein the dimensions refer to the number of neurons comprising the feature map (e.g., the number of neurons along a length, the number of neurons along a width, the number of neurons along a depth, and the number of neurons along a hyper depth of a specified feature map).

In some embodiments, the neurons of the feature maps may compute an output by performing a dot product of received inputs using a set of learned weights (each set of learned weights may herein be referred to as a filter), wherein each received input has a unique corresponding learned weight, wherein the learned weight was learned during training of the CNN.

The transformations/mappings performed by each feature map are indicated by arrows, wherein each type of arrow corresponds to a distinct transformation, as indicated by legend 358. Rightward pointing solid black arrows indicate 3×3×3 convolutions with stride of one, wherein output from a 3×3×3 grid of feature channels of an immediately preceding feature map are mapped to a single feature channel of a current feature map. Each 3×3×3 convolution may be followed by an activation function, wherein, in one embodiment, the activation function comprises a rectified linear unit (ReLU).

Downward pointing hollow arrows indicate 2×2×2 max pooling, wherein the max value from a 2×2×2 grid of feature channels is propagated from an immediately preceding feature map to a single feature channel of a current feature map, thereby resulting in an 8-fold reduction in spatial resolution of the immediately preceding feature map. In some examples, this pooling occurs for each feature independently.

Upward pointing hollow arrows indicate 2×2×2 up-convolutions, which comprise mapping output from a single feature channel of an immediately preceding feature map to a 2×2×2 grid of feature channels in a current feature map, thereby increasing the spatial resolution of the immediately preceding feature map 8-fold.

Rightward pointing dash-tailed arrows indicate copying and cropping of a feature map for concatenation with another, later occurring, feature map. Cropping enables the dimensions of the copied feature map to match the dimensions of the feature map with which the copied feature map is to be concatenated. It will be appreciated that when the size of the first feature map being copied and the size of the second feature map to be concatenated with the first feature map are equal, no cropping may be performed.

Rightward pointing arrows with hollow elongated triangular heads indicate a 1×1×1 convolution, in which each feature channel in an immediately preceding feature map is mapped to a single feature channel of a current feature map, or in other words, wherein a 1-to-1 mapping of feature channels between an immediately preceding feature map and a current feature map occurs.

Rightward pointing arrows with chevron heads indicate incorporation of Gaussian noise into a received input feature map.

Rightward pointing arrows with arcuate hollow heads indicate batch normalization operations, wherein a distribution of activations of an input feature map are normalized.

Rightward pointing arrows with a short hollow triangular head indicates a dropout operation, wherein random or pseudo-random dropout of input neurons (as well as their inputs and outputs) occurs during training.

In addition to the operations indicated by the arrows within legend 358, CNN architecture 300 includes solid filled rectangles corresponding to feature maps, wherein feature maps comprise a height (top to bottom length as shown in FIG. 3, corresponds to a y spatial dimension in an x-y plane), width (not shown in FIG. 3, assumed equal in magnitude to height, corresponds to an x spatial dimension in an x-y plane), and depth (a left-right length as shown in FIG. 3, corresponds to the number of features within each feature channel). Likewise, CNN architecture 300 includes hollow (unfilled) rectangles, corresponding to copied and cropped feature maps, wherein copied feature maps comprise height (top to bottom length as shown in FIG. 3, corresponds to a y spatial dimension in an x-y plane), width (not shown in FIG. 3, assumed equal in magnitude to height, corresponds to an x spatial dimension in an x-y plane), and depth (a length from a left side to a right side as shown in FIG. 3, corresponds to the number of features within each feature channel).

Starting at input image volume 302b (herein also referred to as an input layer), data corresponding to an MR calibration image, such as that shown by MR calibration image 302a, may be input and mapped to a first set of features. In some embodiments, the input data is acquired during a calibration scan that is carried out with a proton density based gradient echo sequence. In some embodiments, the input data is pre-processed (e.g., normalized) before being processed by the neural network. In some embodiments, the input data is magnitude data.

Output layer 356a may comprise an output layer of neurons, wherein each neuron may correspond to a pixel of an anatomical ROI attribute map, and wherein output of each neuron may correspond to a predicted anatomical feature (or lack of the anatomical feature) in a given location within the input MR calibration image. For example, the output of a neuron may indicate whether the corresponding pixel of the anatomical ROI attribute map is part of a knee or is not part of a knee. In another embodiment, output layer 356a may comprise one or more neurons outputting one or more analytical parameter values, which may identify a landmark plane through an analytical description of the plane, e.g., via a plane equation. The values of the parameters of the plane equation(s) may be output by output layer 356a.

As shown in FIG. 3, the landmark map 356b may illustrate one or more landmarks/landmark planes included in the input MR calibration image 302a. The extent of the one or more landmarks/landmark planes is a 3D volume inside the calibration scan volume. The landmarks/landmark planes may be fit/captured by a 3D bounding box, examples of which are shown by first scan region preview 902 and second scan region preview 904, shown in FIG. 9, as well as by the scan box shown in FIG. 10. Further, the one or more landmarks included in landmark map 356b may include a center point that may define the center of the one or more landmarks/landmark planes.

In this way, CNN architecture 300 may enable mapping of an MR calibration image to a predicted landmark map/landmark plane that includes the location and/or other attributes of one or more landmarks/regions of interest. CNN architecture 300 illustrates the feature map transformations which occur as an input image volume is propagated through the neuron layers of the convolutional neural network, to produce the predicted anatomical ROI attribute map.

The weights (and biases) of the convolutional layers in CNN 300 are learned during training, as will be discussed in more detail with reference to FIGS. 6 and 7 below. Briefly, a loss function is defined to reflect the difference between the predicted landmark map output by the CNN 300 and a corresponding ground-truth landmark map. The loss may be back propagated through the layers of the neural network to update the weights (and biases) of the convolutional layers. A plurality of training data pairs, comprising MR calibration images and corresponding ground-truth anatomical ROI attribute maps, may be used to train the neural network 300.

It will be appreciated that the current disclosure encompasses neural network architectures comprising one or more regularization layers, including batch normalization layers, dropout layers, Gaussian noise layers, and other regularization layers known in the art of machine learning which may be used during training to mitigate overfitting and increase training efficiency while reducing training duration. Regularization layers are used during CNN training and deactivated or removed during post training implementation of the CNN. These layers may be interspersed between the layers/feature maps shown in FIG. 3, or may replace one or more of the shown layers/feature maps.

It should be understood that the architecture and configuration of CNN 300 shown in FIG. 3 is for illustration, not for limitation. Any appropriate neural network can be used herein for predicting landmark/landmark plane maps from MR calibration images, such as ResNet, recurrent neural networks, General Regression Neural Network (GRNN), etc. One or more specific embodiments of the present disclosure are described above in order to provide a thorough understanding. These described embodiments are only examples of systems and methods for predicting landmark maps from MR calibration images using a deep neural network. The skilled artisan will understand that specific details described in the embodiments can be modified when being placed into practice without deviating the spirit of the present disclosure.

As appreciated by the MR calibration image 302a, MR calibration images may exhibit large amounts of shading, which may make it difficult to obtain segmentation with classical methods. However, the deep neural network described herein is able to process the calibration images to determine the corresponding landmark map. The resulting location/mask information can then be used to determine one or more diagnostic-scan parameters.

Turning to FIG. 4, a flowchart of an example method 400 for acquiring a diagnostic MR image using diagnostic-scan parameters determined from an MR calibration image is shown. Method 400 may be executed by one or more of the systems discussed above. In one embodiment, MRI system 10 may executed method 400.

Method 400 begins at operation 402, where the MRI system receives an imaging protocol selection from a user. An imaging protocol may indicate one or more anatomy regions of interest to be diagnostically imaged, and may further comprise one or more landmarks spatially related to the one or more anatomy regions of interest. In one example, an MRI system operator may select via a user input device, an imaging protocol for diagnostic imaging of a subject's meniscus plane, wherein the meniscus plane is the anatomy region of interest for the selected imaging protocol, and wherein one or more landmarks spatially related to the meniscus plane may be included in the selected imaging protocol. Further, the imaging protocol may indicate one or more pre-defined image orientations, describing an orientation of an image plane/volume relative to one or more landmarks.

At operation 404, the MRI system acquires an MR calibration image of a patient. MR calibration image acquisition comprises a large FOV, low dose scan, conducted with little or no prior patient positioning. Acquisition of the MR calibration image occurs prior to MRI system calibration, and therefore MR calibration images may include substantial shading/noise. Acquisition of the MR calibration image may, in some embodiments, occur over a period of 5-10 seconds. The MR calibration image comprises a 3D image of an anatomical region of a patient, and therefore an MR calibration image may be regarded as an array of voxels, wherein each voxel may comprise a distinct intensity value in one or more colors.

At operation 406, the MRI system determines diagnostic-scan parameters from the MR calibration image using a trained deep neural network, as discussed in more detail below, with reference to FIG. 500. Briefly, the 3D MR calibration is input into a trained deep neural network, wherein the trained neural network is selected based upon the current imaging protocol selected at operation 402. In some embodiments the trained deep neural network may comprise a 3D convolutional neural network, wherein a plurality of 3D filters are applied to the MR calibration image in order to extract features present in the MR calibration image. The trained deep neural network may then map extracted features to one or more landmark maps/landmark planes. In one embodiment, landmark maps comprise segmentation maps, wherein the segmentation maps indicate a classification of one or more of the plurality of voxels of the input MR calibration image. In another embodiment, the landmark map/landmark planes may be output by the deep neural network in the form of one or more parameters of an analytical expression describing the location of one or more regions/planes (e.g., a plane equation) In one embodiment, the trained deep neural network may produce a binary segmentation map, wherein voxels identified by the deep neural network as belonging to one or more pre-defined landmarks, may be assigned a value of 1 (or some other pre-determined value), and voxels not identified by the deep neural network as belonging to one or more pre-defined landmarks may be assigned a value of 0 (or some other pre-determined value). In some embodiments, landmark maps may comprise multi-label segmentation maps, wherein each voxel of the input MR calibration image is assigned a probability score for each of a pre-determined set of landmarks/classes, wherein a highest probability score may be used to uniquely assigned each voxel to one of the pre-determined set of landmarks/classes.

At operation 408, the MRI system may optionally display a diagnostic-scan region preview to a user. FIG. 9 shows a first diagnostic-scan region preview 902, and a second diagnostic-scan region preview 904, each showing a scan box surrounding/circumscribing an anatomical region of interest to be imaged by a diagnostic-scan. The diagnostic-scan region preview visually depicts for the user (the MRI system operator) the region of patient anatomy to be imaged, thereby enabling the user to assess whether the determined diagnostic-scan parameters are appropriate for the current imaging protocol. In one embodiment, the diagnostic-scan region preview includes a graphical user interface, enabling the MRI system operator to manually reposition a scan box within the imaged volume of the MR calibration image.

At operation 410, the MRI system may determine if the user has accepted the diagnostic-scan region preview. If at operation 410, the user has declined the diagnostic-scan region preview, method 400 may proceed to operation 412, where the user is prompted to reposition the patient and repeat the MR calibration scan. Following operation 412, method 400 may return operation 404, where a second MR calibration image may be acquired, and method 400 may proceed as described previously. However, if at operation 410, the MRI system determines that the user accepted the diagnostic-scan region preview, method 400 may proceed to operation 414.

At operation 414, the MRI system acquires one or more diagnostic images according to the diagnostic-scan parameters determined at operation 406. In one embodiment, the MRI system images a slice within a bore of the MRI system having a location, orientation, and coverage, specified by the diagnostic-scan parameters determined at operation 406. In another embodiment, operation 414 includes acquiring a high-resolution, 3D, isotropic, MR diagnostic image, wherein the location (e.g., center point), orientation (e.g., location of vertices), and coverage (size of the volume) are specified by the diagnostic-scan parameters determined at operation 406.

At operation 416, the MRI system may optionally reformat the diagnostic image acquired at operation 414 based on the one or more scan parameters determined at operation 406. In one embodiment, the imaging protocol selected at operation 402, indicates one or more pre-determined orientations, and at operation 416 the MRI system may produce the one or more pre-determined orientations of the anatomy of interest by taking a planar section through the high-resolution, 3D, isotropic, MR diagnostic image, to produce a high-resolution 2D diagnostic image of the desired orientation.

At operation 418, the MRI system may display the one or more diagnostic images to the user. In one embodiment, the one or more diagnostic images acquired at operation 414 may be displayed to an MRI system operator via a display device. In another embodiment, the reformatted diagnostic images produced at operation 416 are displayed to the MRI system operator via a display device. Following operation 418, method 400 may end.

Turning to FIG. 5, a flowchart of an example method 500 for determining diagnostic-scan parameters from an MR calibration image is shown. Method 500 may be executed by one or more of the systems discussed above. In one embodiment, imaging processing system 31 of MRI system 10 may execute method 500 as part of method 400, as indicated at operation 406.

At operation 502, the image processing system receives an MR calibration image. In one embodiment, the MR calibration image may comprise a 3D image of an anatomical region of a patient. Operation 504 may further include the image processing system receiving an imaging protocol associated with the MR calibration image, wherein the imaging protocol may indicate a set of landmarks to identify within the MR calibration image.

At operation 504, the imagine processing system selects a trained deep neural network based upon the imaging protocol associated with the MR calibration images received at operation 502. In one embodiment, distinct deep neural networks are trained for distinct imaging protocols. In some embodiments, each trained deep neural network may be trained to identify a pre-determined set of landmarks.

At operation 506, the image processing system maps the MR calibration image to a landmark map using the trained deep neural network selected at operation 504. At operation 506 the 3D MR calibration is input into the selected, trained deep neural network. In some embodiments the trained deep neural network may comprise a 3D convolutional neural network, wherein a plurality of 3D filters are applied to the MR calibration image in order to extract features present in the MR calibration image. The trained deep neural network may then map extracted features to one or more landmark maps. In one embodiment, landmark maps comprise segmentation maps, wherein the segmentation maps indicate a classification of one or more of the plurality of voxels of the input MR calibration image. In one embodiment, the trained deep neural network may produce a binary segmentation map, wherein voxels identified by the deep neural network as belonging to one or more pre-defined landmarks, may be assigned a value of 1 (or some other pre-determined value), and voxels not identified by the deep neural network as belonging to the one or more pre-defined landmarks may be assigned a value of 0 (or some other pre-determined value). In some embodiments, landmark maps may comprise multi-label segmentation maps, wherein each voxel of the input MR calibration image is assigned a probability score for each of a pre-determined set of landmarks/classes, wherein a highest probability score may be used to uniquely assigned each voxel to one of the pre-determined set of landmarks/classes.

At operation 508, the image processing system fits/places a scan box within the 3D volume of the MR calibration image based on the landmark map produced at operation 506. In one example, placing the scan box based on the landmark map comprises fitting a scan box size, location, and orientation, to a landmark included in the landmark map, in a manner analogous to fitting of a line to data using linear regression. In one example, the landmark map may comprise a cloud of points (labeled as landmark) to which a 3D plane equation of the form ax+by+cz+d=0 is fit. Based on the parameters a, b, c, and d, the orientation and center point of the scan box may be determined. In another embodiment, the landmark map comprises an analytical expression for one or more planes/regions, and operation 508 comprises determining a position for a scan box based on the analytical expression of one or more planes/regions indicated by the landmark map.

At operation 510, the image processing system determines one or more diagnostic-scan parameters using the scan box placed in operation 508. In one example, the position, orientation, and size of the scan box are correlated with a location, orientation, and coverage, of one or more scan planes within a bore of the MRI system, wherein the scan planes define the region to be imaged by a diagnostic-scan. In another example, based on the extent, position, and orientation of the scan box, the plane equation determined in the example given above, with reference to operation 506, may be used to determine one or more diagnostic parameters, including, number of slices to image the region indicated by the plane, and a diagnostic-scan resolution. Following operation 510, method 500 may end.

Turning to FIG. 6, a flowchart of an example method 600 for training a deep neural network (such as CNN 300 shown in FIG. 3) to determine a landmark map from an MR calibration image is shown. Method 600 may be executed by one or more of the systems discussed above. In some embodiments, method 600 may be implemented by the system 10 shown in FIG. 1 or the system 200 shown in FIG. 2. In some embodiments, method 600 may be implemented by training module 212, stored in non-transitory memory 206 of image processing system 31.

At operation 602, a training data pair, from a plurality of training data pairs, is fed to a deep neural network, wherein the training data pair comprises an MR calibration image (which may be a 3D image comprising a 3D matrix/array of color/intensity values, also referred to as an image volume) and a corresponding ground-truth landmark map. The training data pair may be intelligently selected by the image processing system according to one or more pieces of metadata pertaining to the training data pair. In one embodiment, method 600 may be employed to train a deep neural network (e.g., CNN 300), to identify a set of landmarks associated with a pre-determined imaging protocol, and operation 602 may comprise selecting a training data pair based on the presence or absence of one or more of the landmarks from the set of landmarks, as indicated by the metadata associated with the training data pair.

In some embodiments, the training data pair, and the plurality of training data pairs, may be stored in an image processing system, such as in MR image data 214 of image processing system 31. In other embodiments, the training data pair may be acquired via communicative coupling between the image processing system and an external storage device, such as via Internet connection to a remote server. The MR calibration image of the training data pair may have a large FOV, encompassing one or more landmarks/anatomical regions of interest to be diagnostically imaged. The ground-truth landmark map may include one or more labeled landmarks included in the MR calibration image. In some embodiments, the ground-truth landmark map may comprise a segmentation map, which may comprise a matrix/array of values, wherein each value indicates if a corresponding voxel/pixel or sub-voxel/sub-pixel of the MR calibration image belongs to one or more pre-defined classes, wherein the pre-defined classes may include one or more landmarks, background, noise, or non-landmark anatomical regions. In one embodiment, a landmark map for a 3D MR calibration image may comprise a 3D array of values, wherein identified landmarks are labeled with 1's, and non-landmark regions are labeled with 0's. The training data pairs may be generated according to method 700, discussed in more detail below, with reference to FIG. 7.

At operation 604, the MR calibration image of the training data pair is input into an input layer of the deep neural network, and mapped to a predicted landmark map. As discussed above in reference to operation 602, a landmark map may comprise one or more segmentation maps, which may comprise a matrix/array of values, wherein each value indicates if a corresponding voxel/pixel or sub-voxel/sub-pixel of the MR calibration image belongs to one or more pre-defined classes, wherein the pre-defined classes may include one or more landmarks, background, noise, or non-landmark anatomical region. In some embodiments, each voxel/pixel intensity/color value of the MR calibration image is input into a distinct node/neuron of the input layer of the deep neural network. The output predicted landmark map may comprise a spatial resolution equal or greater than the resolution of the input MR calibration image.

At 606, a difference metric between the predicted landmark map and the ground-truth landmark map is calculated by the image processing system. Said another way, operation 606 comprises determining an error of the predicted landmark map using the ground-truth landmark map, and a loss function. In some embodiments, the difference metric may comprise one or more, or a weighted combination of, a DICE score, a mean square error, an absolute distance error, and an angle error. In some embodiments, operation 606 comprises determining a difference between each output from each output neuron of the deep neural network (wherein the output makes up the values of the predicted landmark map), and a corresponding value in the ground-truth landmark map. In one embodiment, operation 606 may comprise determining a DICE score for the predicted landmark map using the ground-truth landmark map according to the following equation:

$$\text{DICE} = (S \cap T)/(S \cup T),$$

wherein S is the ground-truth landmark map, and T is the predicted landmark map. In some embodiments, both the predicted landmark map and the ground-truth landmark map comprise 3D segmentation maps, wherein one or more landmarks may be labeled via assigning voxels/pixels with values corresponding to one or more landmarks (e.g., labeling each pixel corresponding to a landmark with a first value, and labeling each pixel not corresponding to a landmark with a second value, wherein the first and second value are not equal). In other words, the output of the deep neural network may include, for each voxel of the input MR calibration image, an indication of whether or not that pixel is part of a pre-determined type of landmark (e.g., the knee, the meniscus plane, etc.). The ground-truth landmark map may likewise include an indication, for each pixel of the MR calibration image, whether or not that pixel is part of a pre-determined type of landmark. In some embodiments, the difference calculated at operation 606 may be used in operation 608, while in other embodiments, the difference metric may first be fed to a loss function (e.g., a MSE function, or other loss function known in the art of machine learning), before being used at operation 608.

At operation 608, the weights and biases of the deep neural network are adjusted based on the difference metric (or loss) calculated at operation 606. The difference metric (or loss), may be back propagated through the layers of the deep neural network to update the weights (and biases) of the layers. In some embodiments, back propagation of the loss may occur according to a gradient descent algorithm, wherein a gradient of the loss function (a first derivative, or approximation of the first derivative) is determined for each weight and bias of the deep neural network. Each weight (and bias) of the deep neural network is then updated by adding the negative of the product of the gradient determined (or approximated) for the weight (or bias) and a predetermined step size, according to the below equation:

$$P_{i+1} = P_i - \text{Step}\frac{\partial(\text{loss})}{\partial P_i}$$

Where $P_{i+1}$ is the updated parameter value, $P_i$ is the previous parameter value, Step is the step size, and $$\frac{\partial(\text{loss})}{\partial P_i}$$

is the partial derivative of the loss with respect to the previous parameter.

Following operation 608, method 600 may end. It will be noted that method 600 may be repeated until the weights and biases of the deep neural network converge, a threshold difference metric is obtained (for the training data or on a separate validation dataset), or the rate of change of the weights and/or biases of the deep neural network for each iteration of method 500 are under a threshold. In this way, method 600 enables a deep neural network to be trained to identify one or more landmarks/regions of interest, and to produce landmark maps encoding positional information of the identified landmarks/regions of interest.

Turning to FIG. 7, a flowchart of an example method 700 for generating training data for training a deep neural network to identify one or more landmarks/regions of interest within an MR calibration image is shown. Method 700 may be executed by one or more of the systems discussed above. In one embodiment, MRI system 10 may execute method 700 to generate training data for use in method 600, discussed above.

At operation 702, the image processing system selects an MR calibration image, and a corresponding MR diagnostic image. Both the MR calibration image and the MR diagnostic image are of a same patient, and an anatomical region imaged by the MR calibration image at least partially overlaps with the anatomical region imaged by the MR diagnostic image, that is, both the MR calibration image and the MR diagnostic image include at least some common anatomical structures of the patient, thereby enabling a spatial mapping from the MR diagnostic image space to the MR calibration image space. In some embodiments, both the MR calibration image and the MR diagnostic image are defined within a same coordinate system, thereby enabling direct mapping from positions within the MR diagnostic image to positions within the MR calibration image. In some embodiments, the MR calibration image and corresponding MR diagnostic image are stored in MR image data 214 as a pair. The MR calibration image may comprise a large FOV, low resolution image, whereas the MR diagnostic image may comprise a smaller FOV, higher resolution image.

At operation 704, the image processing system places one or more landmark labels in the MR diagnostic image. In some embodiments, landmark labels may encode positional information of one or more associated landmarks. In some embodiments, landmark labels may be automatically placed within an MR diagnostic image by aligning the MR diagnostic image with an atlas, and projecting positional information (a size, positions, orientation, etc.) of one or more anatomical regions labeled in the atlas, onto the MR calibration image. In some embodiments, an expert may label one or more landmarks within the MR diagnostic image (e.g., by using user input device 32).

At operation 706, the landmark labels placed in the MR diagnostic image are projected/mapped onto the MR calibration image. In some embodiments, both the MR diagnostic image and the MR calibration image are in a same coordinate system, enabling landmark labels placed in the MR diagnostic image to be directly mapped to the MR calibration image, e.g., a voxel at position (1,2,3) labeled as a landmark within the MR diagnostic image may be projected onto the MR calibration image by setting a voxel at position (1,2,3) of the MR calibration image to a pre-determined value indicating the voxel is classified as a landmark. In other embodiments, the MR diagnostic image may be aligned with the MR calibration image by positioning the MR calibration image relative to the MR diagnostic image such that a DICE score between the MR calibration image and MR diagnostic image is minimized, and following alignment, the landmark labels of the MR diagnostic image may be projected onto the MR calibration image, thereby generating a ground-truth landmark map.

At operation 708, the image processing system may store the ground-truth landmark map and the MR calibration image, as a training data pair, within non-transitory memory of the image processing system, or in a communicably coupled storage device. In one embodiment, the image processing system may store metadata along with the training data pair. In some embodiments, the metadata may include an indication of the landmarks within the ground-truth landmark map (e.g., meniscus plane), as well as one or more associated imaging protocols and/or imaging parameters used to acquire the MR diagnostic image from which the ground-truth landmark map was labeled.

Following operation 708, method 700 may end. Method 700 enables an efficient, and in some embodiments automatic, method for generating ground-truth landmark maps for use in training a deep neural network to identify one or more landmarks in MR calibration images. In particular, method 700 enables efficient and accurate placement of landmark labels within a low resolution MR calibration image, by first placing landmark labels in a corresponding high resolution MR diagnostic image, before projecting said labels to the low resolution MR calibration image. In this way, anatomical structures which may be blurry or noisy in the MR calibration image, may be accurately and precisely labeled, thereby enabling the landmark maps produced by the trained deep neural networks taught herein, to have a similar degree of accuracy and precision.

A technical effect of generating ground-truth landmark maps by placing landmark labels in a high resolution MR diagnostic image, aligning the MR diagnostic image with a low resolution MR diagnostic image, and projecting the landmark labels from the MR diagnostic image to the MR calibration image is that, landmark labels may be placed with a greater accuracy and spatial precision than would otherwise be obtainable.

Referring to FIG. 8, examples of ground-truth landmark maps 804, and corresponding high-resolution MR diagnostic images 802, are shown. In some embodiments, ground-truth landmark maps 804 may be generated from corresponding high-resolution MR diagnostic images 802, according to method 700, shown in FIG. 7. Each of the plurality of high-resolution MR diagnostic images 802 has a corresponding low-resolution MR calibration image. As an example, high-resolution MR diagnostic image 806 includes landmark label 808, indicating the position, orientation, size, etc. of a meniscus plane of a knee of a patient. Landmark label 808 may be placed manually by an expert radiologist, or automatically by aligning the high-resolution MR diagnostic image 806 with an atlas, and assigning pixels/voxels of the high-resolution MR diagnostic image 806 overlapping with one or more pre-determined landmarks within the atlas with corresponding landmark labels (e.g., a region of high-resolution MR diagnostic image 806 overlapping with a meniscus plan of an atlas, after alignment of the high-resolution MR diagnostic image with the atlas, may be labeled as a meniscus plane). In a similar manner, the landmark label 808 may be projected from the high-resolution MR diagnostic image 806 to the low-resolution MR calibration image 810, to produce the ground-truth landmark map 812. In some embodiments, the pixels/voxels of both the high-resolution MR diagnostic image 806, and the low-resolution MR calibration image 810, are in a same coordinate system, and therefore each pixel/voxel of the high-resolution MR diagnostic image with a landmark label, may be directly mapped to a corresponding pixel/voxel of the low-resolution MR calibration image.

Turning to FIG. 9, first diagnostic-scan region preview 902 and second diagnostic-scan region preview 904 are shown. First diagnostic-scan region preview 902 and second diagnostic-scan region preview 904 illustrate the position, size and orientation of scan planes used to acquire diagnostic sagittal images. In some embodiments, the position, size and orientation of the scan boxes included in FIG. 9 may be used to determine diagnostic-scan parameters, such as, number of slices, slice thickness, in-plane scan resolution, number of lines of k-space, frequency encoding and phase encoding direction, field of view, center of field of view etc.

Diagnostic-scan region previews, such as first diagnostic-scan region preview 902 and second diagnostic-scan region preview 904, may be generated by fitting a scan box based on the position, location, orientation, and size, of one or more landmarks indicated by a landmark map. In the embodiments shown in FIG. 9, the scan boxes of the first diagnostic-scan region preview 902, and the second diagnostic-scan region preview 904, are aligned with the posterior end of the Femoral Condyles (as indicated by the dotted line in first diagnostic-scan region preview 902) and meniscus plane (as shown in second diagnostic-scan region preview 904). The width (left right extent) of the scan boxes may be based upon the lateral extent of the Femoral condyle bone, as shown in both first diagnostic-scan region preview 902 and second diagnostic-scan region preview 904. In addition, the scan boxes indicate the coverage of a corresponding diagnostic image, wherein, in the example shown in FIG. 9, the scan boxes indicate that the diagnostic sagittal image should have sufficient coverage along superior-inferior to include regions superior to patella and patellar tendon in inferior side (superior-inferior coverage shown in first diagnostic-scan region preview 904). Further, the scan boxes in first diagnostic-scan region preview 902 and second diagnostic-scan region preview 904 indicate the an extent of a corresponding diagnostic image in the anterior-posterior direction, wherein, in the example shown in FIG. 9, the diagnostic-scan should cover the entire knee, including patella in the anterior direction and the knee muscles in the inferior direction (anterior-posterior coverage shown in first diagnostic-scan region preview 902).

In some embodiments, scan region previews may be displayed to an MRI system operator for approval, prior to execution of a diagnostic-scan based on one or more scan parameters determined from the scan box displayed in the diagnostic-scan region preview.

Turning to FIG. 10, an MR calibration image 1002, a corresponding landmark map 1004, a scan box 1006 fit to landmark map 1004, and a diagnostic image 1008 acquired based on the scan box 1006, are shown. In one embodiment, MR calibration image 1002 may be acquired by an MRI system, such as MRI system 10, as part of one or more methods herein disclosed, e.g., at operation 404 of method 400. As can be seen, MR calibration image 1002 comprises a large FOV, low resolution, MR image of a knee of a patient. MR calibration image 1002 may be fed to a trained deep neural network, such as CNN 300, which may be trained according to one or more of the steps of method 600, discussed above.

The trained deep neural network may automatically map the MR calibration image 1002 to landmark map 1004, wherein the meniscus plane of the knee is identified by a mask/map, overlaid on the MR calibration image 1004. The landmark map 1004 may be used to position a scan box 1006, to capture one or more anatomical regions of interest. The one or more anatomical regions of interest may, in some embodiments, have a fixed spatial relationship with the one or more landmarks identified in landmark map 1004. In some embodiments, the landmarks themselves may be the anatomical region of interest to be imaged, while in other embodiments, the anatomical region of interest may not include the landmark (the landmark in such cases is simply used to determine a location of the region of interest using the fixed spatial relationship between the landmark and the region of interest). In some embodiments, the scan box may be positioned based on both the landmark location (e.g., center of the landmark as indicated by the landmark map) as well as input received via a user input device, which may, in some examples, indicate a width of the landmark, a distance from the center point to be imaged, etc.

The scan box 1006 may be used to set one or more diagnostic-scan parameters of an MRI system, and a diagnostic-scan may occur according to the diagnostic-scan parameters to generate an MR diagnostic image, such as MR diagnostic image 1010. As can be seen the FOV of MR diagnostic image 1010 comprises the FOV indicated by scan box 1006, clearly showing the anatomical region of interest (e.g., the meniscus plane of the knee).

When introducing elements of various embodiments of the present disclosure, the articles "a," "an," and "the" are intended to mean that there are one or more of the elements. The terms "first," "second," and the like, do not denote any order, quantity, or importance, but rather are used to distinguish one element from another. The terms "comprising," "including," and "having" are intended to be inclusive and mean that there may be additional elements other than the listed elements. As the terms "connected to," "coupled to," etc. are used herein, one object (e.g., a material, element, structure, member, etc.) can be connected to or coupled to another object regardless of whether the one object is directly connected or coupled to the other object or whether there are one or more intervening objects between the one object and the other object. In addition, it should be understood that references to "one embodiment" or "an embodiment" of the present disclosure are not intended to be interpreted as excluding the existence of additional embodiments that also incorporate the recited features.

In addition to any previously indicated modification, numerous other variations and alternative arrangements may be devised by those skilled in the art without departing from the spirit and scope of this description, and appended claims are intended to cover such modifications and arrangements. Thus, while the information has been described above with particularity and detail in connection with what is presently deemed to be the most practical and preferred aspects, it will be apparent to those of ordinary skill in the art that numerous modifications, including, but not limited to, form, function, manner of operation and use may be made without departing from the principles and concepts set forth herein. Also, as used herein, the examples and embodiments, in all respects, are meant to be illustrative only and should not be construed to be limiting in any manner.

The invention claimed is:

1. A method, comprising:

training a deep neural network to map magnetic resonance (MR) calibration images to landmark maps;

receiving a particular MR calibration image;

determining, from the particular MR calibration image, a corresponding landmark map using the trained deep neural network, the landmark map comprising a cloud of points labeled as a landmark;

determining one or more diagnostic-scan parameters based on a scan box placed on the landmark map without use of localizer images, wherein a size, a location, and an orientation of the scan box is fit to the landmark on the landmark map based on the cloud of points;

acquiring an MR diagnostic image according to the one or more diagnostic-scan parameters; and displaying the MR diagnostic image via a display device.

2. The method of claim 1, wherein training the deep neural network comprises feeding a training data pair to the deep neural network, wherein the training data pair includes an MR calibration image and a corresponding ground-truth landmark map, wherein calibration image resolution is lower than localizer image resolution, and wherein a resolution of the MR calibration image is the calibration image resolution.

3. The method of claim 2, wherein training the deep neural network comprises:

mapping the MR calibration image in the training data pair to a predicted landmark map using the deep neural network;

calculating a difference metric between the predicted landmark map and the ground-truth landmark map; and adjusting parameters of the deep neural network via backpropagation based on the difference metric.

4. The method of claim 2, wherein the ground-truth landmark map is generated by:

selecting the MR calibration image and a corresponding MR diagnostic image;

placing landmark labels in the corresponding MR diagnostic image; and projecting the landmark labels from the corresponding MR diagnostic image onto the MR calibration image to produce the ground-truth landmark map.

5. The method of claim 4, wherein placing landmark labels in the corresponding MR diagnostic image comprises aligning one or more anatomical regions of the corresponding MR diagnostic image with an atlas, and assigning landmark labels to one or more landmarks of the corresponding MR diagnostic image using the atlas.

6. The method of claim 1, wherein the one or more diagnostic-scan parameters determined include image resolution.

7. The method of claim 1, wherein the scan box is fit via 3D plane equation $ax+by+cz+d=0$ using the cloud of points.

* * * * *